United States Patent
Halas et al.

(10) Patent No.: US 7,144,627 B2
(45) Date of Patent: Dec. 5, 2006

(54) MULTI-LAYER NANOSHELLS COMPRISING A METALLIC OR CONDUCTING SHELL

(75) Inventors: Nancy J. Halas, Houston, TX (US); Corey J. Radloff, Houston, TX (US)

(73) Assignee: William Marsh Rice University, Houston, TX (US)

( * ) Notice: Subject to any disclaimer, the term of this patent is extended or adjusted under 35 U.S.C. 154(b) by 752 days.

(21) Appl. No.: 10/013,259

(22) Filed: Nov. 5, 2001

(65) Prior Publication Data
US 2002/0187347 A1    Dec. 12, 2002

Related U.S. Application Data

(63) Continuation-in-part of application No. 09/966,544, filed on Sep. 27, 2001, now abandoned, and a continuation-in-part of application No. 09/965,305, filed on Sep. 27, 2001, now abandoned, which is a continuation-in-part of application No. 09/038,377, filed on Mar. 11, 1998, now Pat. No. 6,344,272.

(60) Provisional application No. 60/245,530, filed on Nov. 3, 2000, provisional application No. 60/245,531, filed on Nov. 3, 2000, provisional application No. 60/237,520, filed on Oct. 4, 2000, provisional application No. 60/237,215, filed on Oct. 2, 2000, provisional application No. 60/235,816, filed on Sep. 27, 2000, provisional application No. 60/040,570, filed on Mar. 14, 1997, provisional application No. 60/040,971, filed on Mar. 12, 1997.

(51) Int. Cl.
 *B32B 5/16* (2006.01)
(52) U.S. Cl. .................... 428/403; 428/570; 977/773
(58) Field of Classification Search ............... 428/570, 428/403, 404, 407; 977/DIG. 1
See application file for complete search history.

(56) References Cited

U.S. PATENT DOCUMENTS

| | | | | |
|---|---|---|---|---|
| 5,322,798 A | * | 6/1994 | Sadowski | 436/113 |
| 6,180,415 B1 | * | 1/2001 | Schultz et al. | 436/518 |
| 6,344,272 B1 | * | 2/2002 | Oldenburg et al. | 428/403 |
| 6,428,811 B1 | * | 8/2002 | West et al. | 424/497 |
| 6,530,944 B1 | * | 3/2003 | West et al. | 607/88 |
| 6,660,381 B1 | * | 12/2003 | Halas et al. | 428/403 |
| 6,685,986 B1 | * | 2/2004 | Oldenburg et al. | 427/214 |
| 6,699,724 B1 | * | 3/2004 | West et al. | 436/525 |
| 6,773,823 B1 | * | 8/2004 | O'Connor et al. | 428/548 |

OTHER PUBLICATIONS

Diao et al, "Electromagnetic cavity resonant absorption of the gold nanoshell", J. Phys. D: Appl. Phys. 34 No. 14 (Jul. 21, 2001) L79-L82.*

(Continued)

*Primary Examiner*—H. Thi Le
(74) *Attorney, Agent, or Firm*—Conley Rose, P.C.

(57) ABSTRACT

Composite particles containing metallic shell layers are provided. The particles may include a coating layer, such as of a protective or electrically non-conducting material, over an outermost metallic shell layer. The particle preferably has a plasmon resonance associated with at least one metallic shell layer. The coating layer preferably imparts improved thermal stability to the plasmon resonance. Further, the present invention relates to particles that include at least two metallic shell layers, separated by a coating layer. The addition of a second metallic shell layer preferably allows the plasmon resonance of the shell layer to be more red-shifted with respect to a colloidal particle of the metal that the plasmon resonance of a particle of the same size but with only a single metallic shell.

39 Claims, 5 Drawing Sheets

OTHER PUBLICATIONS

Baer, The Hebrew University of Jerusalem; Neuhauser and Weiss, Dept. of Chem and Biochem, U. of California, "Enhanced Absorption Induced by a Metallic Nanoshell", (2004).*

Teperik et al., "Radiative decay of plasmons in a metallic nanoshell", Physical Review B 69, 155402 (2004).*

Radloff, C. et al; *Enhanced Thermal Stability of Silica-Encapsulated Metal Nanoshells*; Applied Physics Letters; vol. 79, No. 5, Jul. 30, 2001; pp. 674-676.

Ung, T., et al; *Controlled Method for Silica Coating of Silver Colloids. Influence of Coating on the Rate of Chemical Reactions*; Langmuir 1998, 14, pp. 3740-3748.

Liz-Marzán, L.M., et al; *Synthesis of Nanosized Gold—Silica Core-Shell Particles*; Langmuir 1996, 12, pp. 4329-4235.

* cited by examiner

Sweep Core size 300-450 nm in 25 nm increments
15/60/5 nm Au/Si/Au shells

Sweep Core size 500-800, 1000 nm in 100 nm increments
15/60/5 nm Au/Si/Au shells Sweep Core size 500-800, 1000 nm in 100 nm increments
15/200/5 nm Au/Si/Au shells

MULTI-LAYER NANOSHELLS COMPRISING A METALLIC OR CONDUCTING SHELL

CROSS-REFERENCE TO RELATED APPLICATIONS

This application claims the benefit of Provisional Applications Ser. No. 60/245,530, filed Nov. 3, 2000 and Ser. No. 60/245,531, filed Nov. 3, 2000. Further, this application is a continuation-in-part of U.S. Utility application Ser. No. 09/038,377, filed Mar. 11, 1998, now U.S. Pat. No. 6,344,272, which claims the benefit of U.S. Provisional Applications Ser. No. 60/040,971, filed Mar. 12, 1997 and Ser. No. 60/040,570, filed Mar. 14, 1997. Still further, this application is a continuation-in-part of U.S. Utility applications Ser. No. 09/966,544, filed Sep. 27, 2001, now abandoned, and Ser. No. 09/965,305, filed Sep. 27, 2001, now abandoned, each of which claims the benefit of U.S. Provisional Applications Ser. No. 60/235,816, filed Sep. 27, 2000, Ser. No. 60/237,215, tiled Oct. 2, 2000, and Ser. No. 60/237,520, filed Oct. 4, 2000. Each of the above-listed applications is hereby incorporated herein by reference.

STATEMENT REGARDING FEDERALLY SPONSORED RESEARCH OR DEVELOPMENT

Funding from Office of Naval Research Grant Number N00014-98-0393 supported this work.

FIELD OF THE INVENTION

The present invention relates generally to composite particles containing metallic shell layers. More particularly, the present invention relates to particles that include a coating layer, such as of a protective or electrically non-conducting material, over an outermost metallic shell layer. Further, the present invention relates to particles that include at least two metallic shell layers, separated by a coating layer.

BACKGROUND OF THE INVENTION

Particles able to absorb or scatter light of well-defined colors have been used in applications involving detection, absorption, or scattering of light, for example medical diagnostic imaging. Such particles are typically colloidal metal particles. The term colloidal conventionally refers to the size of the particles, generally denoting particles having a size between about 1 nanometer and about 1 micron.

Small particles made from certain metals that are in the size range of colloidal metal particles tend to have a particularly strong interaction with light, termed a resonance, with a maximum at a well-defined wavelength. Such metals include gold, silver, platinum, and, to a lesser extent, others of the transition metals. Light at the resonance wavelength excites particular collective modes of electrons, termed plasma modes, in the metal. Hence the resonance is termed the plasmon resonance.

By selecting the metal material of a colloidal particle, it possible to vary the wavelength of the plasmon resonance. When the plasmon resonance involves the absorption of light, this gives a solution of absorbing particles a well-defined color, since color depends on the wavelength of light that is absorbed. Solid gold colloidal particles have a characteristic absorption with a maximum at 500–530 nanometers, giving a solution of these particles a characteristic red color. The small variation in the wavelength results from a particle size dependence of the plasmon resonance. Alternatively, solid silver colloidal particles have a characteristic absorption with a maximum at 390–420 nanometers, giving a solution of these particles a characteristic yellow color.

Using small particles of various metals, particles can be made that exhibit absorption or scattering of selected characteristic colors across a visible spectrum. However, a solid metal colloidal particle absorbing in the infrared is not known. Optical extinction, in particular absorption or scattering, in the infrared is desirable for imaging methods that operate in the infrared. Further, optical communications, such as long distance phone service that is transmitted over optical fibers, operate in the infrared.

It has been speculated since the 1950's that it would be theoretically possible to shift the plasmon resonance of a metal to longer wavelengths by forming a shell of that metal around a core particle made of a different material. In particular, the full calculation of scattering from a sphere of arbitrary material was solved by Mie, as described in G. Mie, Ann. Phys. 24, 377 (1908). This solution was extended to concentric spheres of different materials, using simplifying assumptions regarding the dielectric properties of the materials, by Aden and Kerker, as described in A. L. Aden and M. Kerker, J. of Applied Physics, 22, 10, 1242 (1951). The wavelength of the plasmon resonance would depend on the ratio of the thickness of the metal shell to the size, such as diameter of a sphere, of the core. In this manner, the plasmon resonance would be geometrically tunable, such as by varying the thickness of the shell layer. A disadvantage of this approach was its reliance on bulk dielectric properties of the materials. Thus, thin metal shells, with a thickness less than the mean free path of electrons in the shell, were not described.

Despite the theoretical speculation, early efforts to confirm tunability of the plasmon resonance were unsuccessful due to the inability to make a particle having a metal shell on a dielectric core with sufficient precision so as to have well-defined geometrical properties. In these earlier methods, it was difficult to achieve one or both of monodispersity of the dielectric core and a well-defined controllable thickness of a metal shell, both desirable properties for tuning the plasmon resonance. Thus, attempts to produce particles having a plasmon resonance in keeping with theoretical predictions tended to result instead in solutions of those particles having broad, ill-defined absorption spectra. In many instances this was because the methods of making the particles failed to produce smooth uniform metal shells.

Further, an anticipated difficulty in application of particles having metal shells is their susceptibility to loss of structure under heating. Thus, methods of protecting particles having metal shells are desired. Still further, due to material and size constraints, it is anticipated to be difficult to extend the plasmon resonance of a particle with a single shell into the mid and far infrared.

Thus there remains a need for improved plasmon resonant particles and methods of making them.

SUMMARY OF THE INVENTION

According to a preferred embodiment, the present invention features a nanoparticle that includes a core, a metallic shell layered on the core, and a coating layered on the shell.

According to another preferred embodiment, the present invention features a nanoparticle that includes a core, a shell surrounding the core, and a protective coating surrounding said shell, where the shell includes a metal selected from among silver, gold, nickel, copper, iron, platinum, and palladium.

According to any one of the above-described embodiments, the nanoparticle preferably has a plasmon resonance associated with the metallic shell. Further, the plasmon resonance preferably has improved thermal stability with respect to a comparable nanoparticle excluding said coating. Still further, the coating is preferably sufficiently thick such that the peak wavelength of the plasmon resonance is stable within about 3% to at least about 300° C., more preferably to at least about 600° C.

According to an alternative preferred embodiment, the present invention features a nanoparticle that includes a core, a first metallic shell layered on the core, a coating layered on the shell, and a second metallic shell layered on said coating.

According to yet another preferred embodiment of the present invention, a nanoparticle includes a plurality of conducting shells, where at least one adjacent pair of shells is separated by a non-conducting layer, and where each non-conducting layer includes a material selected from among silicon dioxide, titanium dioxide, polymethyl methacrylate, polystyrene, gold sulfide, cadmium selenium, cadmium sulfide, gallium arsenide, and dendrimers.

According to any one of the last two above-described embodiments, the nanoparticle preferably has a first plasmon resonance associated with the first shell, and a second plasmon resonance associated with the second shell. Further, the coating preferably has sufficient thickness such that the second plasmon resonance is spectrally distinct from the first plasmon resonance. Alternatively or in combination, the second plasmon resonance preferably has a peak position between about 300 nanometers and about 20 microns, more preferably between about 0.7 microns and about 20 microns.

Thus, the present invention comprises a combination of features and advantages which enable it to overcome various problems of prior particles. The various characteristics described above, as well as other features, will be readily apparent to those skilled in the art upon reading the following detailed description of the preferred embodiments of the invention, and by referring to the accompanying drawings.

BRIEF DESCRIPTION OF THE DRAWINGS

For a more detailed description of the preferred embodiment of the present invention, reference will now be made to the accompanying drawings, wherein.

DETAILED DESCRIPTION OF THE PREFERRED EMBODIMENT

Multi-Layer Nanoshells

Figure 1:
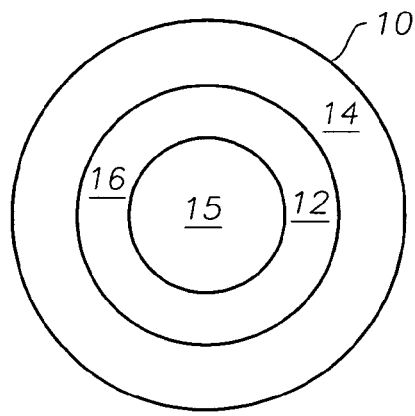
FIG. 1 is a cross-sectional view of a particle according to an embodiment of the present invention.

Referring initially to FIG. 1, according to a preferred embodiment of the present invention, a particle 10 includes a subparticle 12 and a coating 14. Subparticle 12 preferably includes a core 15 and a shell 16. Particle 10 is preferably a nanoparticle. In particular, particle 10 preferably has a size between about 1 nanometer and about 5 microns. Particle 10 is preferably spherical in shape. Alternatively, particle 10 may have any geometrical shape, such as cubical, cylindrical, hemispherical, elliptical, and the like. The size of particle 10 is preferably defined by the average diameter of particle 10.

The average diameter of an object, such as particle 10, having a surface defining the extent of the object is defined herein as the angular average of the distance between opposing regions of the surface through a fixed point located interior to the object. For an object embedded in three dimensions, described for example by a radial coordinate system centered at the fixed point, the average is over both the radial angle $\theta$ and the aziumuthal angle $\phi$. That is, the average diameter $<D>$ of the diameter $D(\theta, \phi)$ is given by $<D>=(\int d\theta d\phi D(\theta, \phi))/4\pi^2$.

Core 15 is preferably spherical. Alternatively, core 15 may have any geometrical shape, such as cubical, cylindrical, hemispherical, elliptical, and the like. The size of core 15 is preferably defined by the average diameter of core 15. Core 15 preferably has a size between about 1 nanometer and about 5 microns, more preferably between about 10 nanometers and about 4 microns.

Core 15 preferably includes a substrate material. The substrate material is preferably any material that has a smaller dielectric permittivity than preferred materials for shell 16, described further below. The substrate material is preferably a dielectric material. Alternatively, or in combination, core 15 may include a semiconducting material. Further, many dielectric materials are also semiconducting. Suitable substrate materials include silicon dioxide (also termed silica), titanium dioxide, polymethyl methacrylate, polystyrene, gold sulfide. cadmium sulfide, cadmium sulfide, gallium arsenide, and the like. Further, suitable substrate materials include dendrimers. In some embodiments, the substrate material extends throughout core 15, such that core 15 primarily contains the substrate material. Alternatively, in some other embodiments, the substrate material is arranged as a surface layer of core 15.

Shell 16 is preferably layered on core 15. In particular, shell 16 preferably primarily extends outwards, for example in a radial direction, from core 15. In some embodiments, the inner surface of shell 16 contacts the outer surface of core 15. The contact between core 15 and shell 16 may occur between portions of core 15 and shell 16. Alternatively, shell 16 and core 15 may be in continuous contact.

Shell 16 preferably includes inner and outer surfaces that each are spherical. Alternatively, shell 16 may be defined by inner and outer surfaces where one or both surfaces has an alternative shape, such as cubical, cylindrical, hemispherical, elliptical, and the like. Each surface is preferably closed. The thickness of shell 16 preferably is defined as the difference between the outer radius and the inner radius, computed by subtracting the inner radius from the outer radius. The inner radius is half the average diameter of the inner surface. Likewise, the outer radius is half the average diameter of the outer surface.

Shell 16 preferably includes a metallic material. In some embodiments, the metallic material includes at least one element selected from the Periodic Table of the Elements that are commonly known as metals. The metallic material may include primarily a single element. Alternatively, the metallic material may be a combination of at least two elements, such as an alloy, for example a binary alloy. As used herein, metals include those elements disclosed in the USPTO Manual of Classification as metals. Both the old IUPAC notation, with Roman numerals, and the new notation, with Arabic numbers will be used herein. See, for example Lewis, Richard J., Sr., "Hawley's Condensed Chemical Dictionary" (1997, John Wiley and Sons), the inside front cover page, hereby incorporated herein by reference, for a comparison of notations. In particular, Group I metals include Group 1 metals (Li, Na, K, Rb, Ca, and Fr) and Group 11 metals (Cu, Ag, and Au). Group II metals include Group 2 metals (Be, MG, Ca, Sr, Ba, and Ra) and Group 12 metals (Zn, Cd, and Hg). Group III metals include Group 3 metals (Sc and Y) and Group 13 metals (Al, Ga, In, and Tl). Group IV metals include Group 4 metals (Ti, Zr, and Hf) and Group 14 metals (Ge, Sn, and Pb). Group V metals include Group 5 metals (V, Nb, and Ta) and Group 15 metals (As, Sb, and Bi). Group VI metals include Group 6 metals (Cr, Mo, and W) and Group 16 metals (Po). Group VII metals include Group 7 metals (Mn, To, and Re). Group VIII metals include Group 8 metals (Re, Ru, and Os), Group 9 metals (Co, Rh, and Ir), and Group 10 metals (Ni, Pd, and Pt). A metallic material forming shell 16 preferably is selected from the elements of Groups I and VIII. More preferably, the metallic material is selected from among copper (Cu), silver (Ag), gold (Au), nickel (Ni), platinum (Pt), palladium (Pd), and iron (Fe). Alternatively, in some embodiments, the metallic material includes a synthetic metal. A synthetic metal is defined herein as an organic or organometallic material that has at least one characteristic property in common with a metal. For example, the property may be electrical conductivity. Thus, synthetic metals include conducting polymers, such as polyacetylene, polyanaline, and the like. Therefore, when shell 16 is metallic, shell 16 may include any of an elemental metal, an alloy, a synthetic metal, and combinations thereof.

Referring still to FIG. 1, in some embodiments, an intermediate material (not shown) is disposed between shell 16 and core 15. This intermediate material may have any suitable function.

Figure 2:
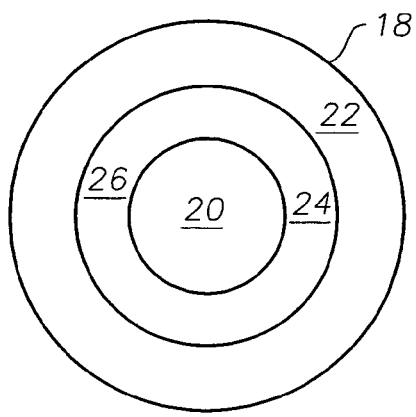
FIG. 2 is a cross-sectional view of a subparticle according to an embodiment of the present invention.

Referring now to FIG. 2, according to an embodiment of the present invention, a subparticle 18 includes a core 20, a metallic shell 22, and an intermediate layer 24. Layer 24 preferably includes a functionalizing material that is adapted to bind to a shell 22. Thus, the presence of the intermediate layer functionalizes the core, allowing a metallic material to be coated directly onto the surface of functionalized core 26 formed by core 20 and layer 24.

According to an embodiment of the present invention, the functionalizing material is a metallic material adapted to receive the primary metallic material forming shell 22, for example by reduction of primary metallic material onto the functionalizing material. The functionalizing material is preferably tin. Alternatively, titanium, which has similar reduction properties to tin, could be used in replacement of tin. A portion of the functionalizing material forming layer 24 is preferably the reaction product of ions of the functionalizing material with hydroxyl groups at the surface of a silica core. Additional functionalizing material forming layer 24 is preferably the reaction product of reduction from solution of additional ions of the functionalizing material onto the functionalizing material bound to the core.

According to an alternative embodiment, the functionalizing material is a nonmetallic material. The nonmetallic material may be selected from among CdS, CdSe, and the like.

According to still an alternative embodiment, intermediate layer 24 includes a plurality of linker molecules. The linker molecules are arranged such that one end of each linker molecule binds to core 15 and the other end of each linker molecule binds to shell 16. Thus, preferably one end of a linker molecule preferably includes a first functional group with an affinity for material contained in core 15 and the other end of the linker molecule preferably includes a second functional group with an affinity for material contained in shell 16. Aminopropylsilanetriol is a linker molecule that is suited to linking a metallic shell to a silica core. Aminopropylsilanetriol is the hydrolyzed form of aminopropyltriethoxysilane (APTES). The silanol groups at one end of aminopropylsilanetriol have an affinity for silica, in particular hydroxyl groups at the surface of silica. Thus, a silanol linkage between core 20 and aminopropylsilanetriol is derived from the reaction of a silanol group of aminopropylsilanetriol with a hydroxyl group on core 20, with elimination of water. An amino group at the other end of aminopropylsilanetriol has an affinity for metallic materials. Thus, an amino linkage between shell 22 and aminopropylsilanetriol is derived from the reaction of aminopropylsilanetriol with shell 22.

It will be understood that alternative linker molecules may be used. For example, the linker molecule may include an end group with an affinity for metallic material that includes an active atomic site that is an element selected from among sulfur and phosphorus, as alternatives to nitrogen. For example, a linker molecule having a nitrogen as an atomic site may be the hydrolyzed form of any suitable amino silane, such as aminopropyltrimethoxy silane, diaminopropyl-diethoxy silane, 4-aminobutyldimethylmethoxy silane, and the like. Further, a linker molecule having a sulfur as an atomic site may be the hydrolyzed form of any suitable thio silane, such as mercaptopropyltrimethoxy silane, and the like.

Figure 3:
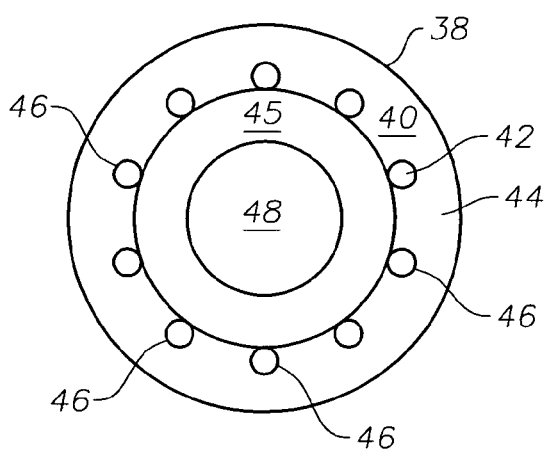
FIG. 3 is a cross-sectional view of a subparticle according to an alternative embodiment of the present invention.

Referring now to FIG. 3, in some embodiments, a subparticle 38 includes a shell 40 that includes a precursor metallic material 42 that may be different in chemical make-up from a primary metallic material 44 that primarily forms shell 40. Precursor material 42 provides nucleation sites for the formation of shell 40. Precursor material 42 preferably includes colloidal particles 46 distributed over the surface of core 48. Thus, colloidal particles 46 may be embedded as part of shell 40. Colloidal particles 46 preferably are bound to intermediate layer 45. For example, in some embodiments, colloidal particles 46 are bound to linker molecules in intermediate layer 45. Thus, for example, gold colloidal particles may bind to aminopropylsilanetriol and serve as nucleation sites for a silver shell. Alternatively, tin colloidal particles may extend from an intermediate layer 45 that includes tin. In an exemplary arrangement, as disclosed in U.S. Utility application Ser. No. 09/966,544, filed September 27, which is incorporated herein by reference, subparticles were made including gold colloidal precursor particles having a size between about 1 and about 3 nanometers that served as nucleation site for a silver shell having a thickness between about 10 nanometers and about 20 nanometers. It been observed that, for this arrangement, the plasmon resonance associated with the silver shell was well-described by neglecting the presence of the gold colloids.

Referring again to FIG. 1, in some embodiments, particle 10 has a plasmon resonance associated with shell 16. A plasmon resonance conventionally is a resonant interaction of electromagnetic radiation with collectively coupled electrons. In a conductive metallic material, the electrons that interact are the conduction electrons. A plasmon resonance is preferably detected as a peak in a spectrum. The spectrum may be an absorption spectrum. Alternatively, the spectrum may be a scattering spectrum. Further, the spectrum is preferably visualized as a plot of intensity as a function of wavelength. Intensity may be measured, as is conventional, in arbitrary units. Wavelength may be measured in any suitable units, such as nanometers, microns, and the like. Further, the plot may be a plot of intensity as a function of any other spectroscopic variable, such as wavenumber (e.g. $cm^{-1}$ and the like) and frequency (e.g. mHz and the like). A wavelength $\lambda$, wavenumber n, and frequency v are conventionally related as $\lambda = v_r/v = 1/n$, where $v_r$ is the velocity of propagation of the radiation. For propagation in a vacuum, $v_r = c$, the speed of light. When the spectrum is an absorption spectrum the intensity is the intensity of radiation that is absorbed, such as by particle 10 or a plurality of particles 10. Likewise, when the spectrum is a scattering spectrum the intensity is the intensity of radiation that is scattered, such as by particle 10 or plurality of particles 10.

Figure 4:
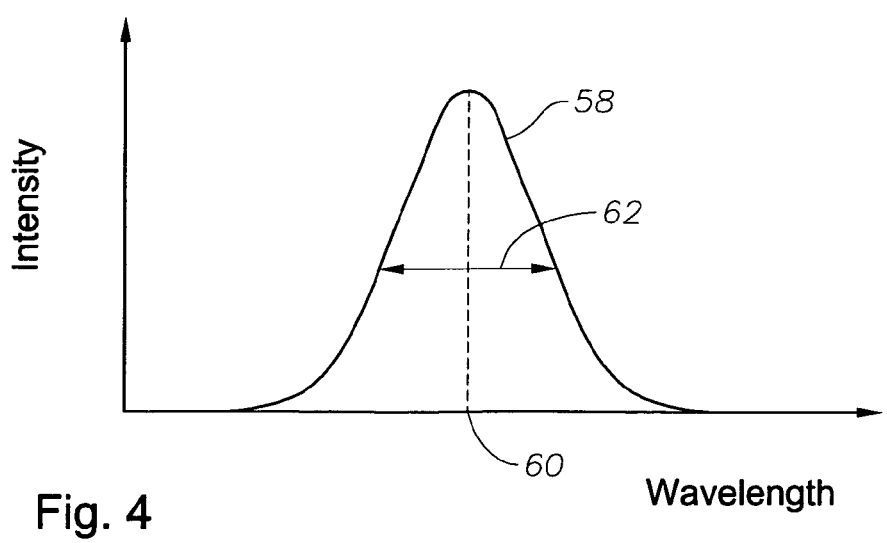
FIG. 4 is a schematic plot of a spectrum associated with the particle as shown in FIG. 1.

Referring now to FIG. 4, a plasmon resonance peak 58 preferably has a peak wavelength 60 and a peak width 62. Peak wavelength 60 is the wavelength at which plasmon resonance peak 58 has a maximum. Peak width 62 is herein defined as the full width half maximum of plasmon resonance peak 58. Peak width 62 may include contributions from both homogenous and inhomogeneous line broadening. Homogeneous line broadening occurs in part as a result of electron collisions. Peak width 62 then depends in part on the shell electron mean free path.

Peak wavelength 60 preferably is shifted from the peak wavelength of a colloidal particle made of the same material as the primary material forming shell 16. The shift is preferably a red-shift, that is a shift to larger wavelength. Peak wavelength 60 is preferably between about 300 nanometers and about 20 microns.

Gold and silver are exemplary metallic materials for use in shell 16 such that particle 10 has a plasmon resonance associated with shell 16. When shell 16 includes silver, nanoparticle 10 preferably has a plasmon resonance with a peak wavelength from about 400 nanometers to about 20 microns. In contrast, the peak wavelength for colloidal silver varies from about 390–420 nanometers depending on the size of the colloids, giving a solution of silver colloids a characteristic yellow color. Thus, when shell 16 contains silver, peak wavelength 60 is preferably red-shifted from colloidal silver. Similarly, when shell 16 includes gold, nanoparticle 10 preferably has a plasmon resonance with a peak wavelength greater than about 500 nanometers to about 20 microns. In contrast, the peak wavelength for colloidal gold varies from about 500–530 nanometers depending on the size of the colloids, giving a solution of gold colloids a characteristic red color. Thus, when shell 16 contains gold, peak wavelength 60 is preferably red-shifted from colloidal gold.

In some embodiments, shell 16 has a thickness less than the bulk electron mean free path of the primary material forming shell 16. When the thickness of shell 16 is greater than or equal to the bulk electron mean free path, that is the value of the mean free path in a bulk amount of the material forming shell 16, the shell electron mean free path is equal to the bulk electron mean free path. When the thickness of shell 16 is less than the bulk electron mean free path, the shell electron mean free path is equal to the thickness of shell 16. Thus, when the thickness of shell 16 is less than the bulk electron mean free path, size-dependent effects are present in the peak width 62.

Shell 16 is preferably uniform. Inhomogeneous line broadening may occur in part due to nonuniformity of shell 16. Nonuniformity may arise from variations in the local distance between the inner surface and the outer surface of shell 16. Thus, in some parts of a nonuniform shell the local distance differs from the shell thickness (i.e. the average distance). The variations in local distance for shell 16 are preferably less than about 20%, more preferably less than about 10%.

A plurality of cores 14 and a plurality of particles 10 each is preferably substantially monodisperse. Further, inhomogeneous broadening in a plasmon resonance originating from a plurality of particles 10 may also occur in part due to polydispersity of particles 10. That is, inhomogeneous broadening may arise from variations in the size of particles 10. In a preferred embodiment, a plurality of cores 14 is characterized by a distribution of sizes with a standard deviation of up to about 20%, more preferably up to about 10%.

Shell 16 is preferably a complete shell. Alternatively, shell 16 is a partial shell, also termed an incomplete shell. A complete shell extends substantially continuously between the inner surface and the outer surface of shell 16. Thus, a complete shell completely surrounds core 15, encapsulating core 15. Completeness of shell 16 may be observed in a plasmon resonance of particle 10 that is associated with shell 16. In particular, when shell 16 is complete, the peak wavelength of the plasmon resonance is related to the geometry of particle 10, specifically, to the ratio of the thickness of shell 16 to the size of core 15. As shell 16 increases in thickness, the peak wavelength of particle 10 shifts to shorter wavelengths. Thus, the progress of a reaction forming shell 16 may be followed spectrophotometrically and terminated when a desired peak wavelength is obtained.

Coating 14 is preferably layered on shell 12. In particular, core 16 preferably primarily extends outwards, for example in a radial direction, from shell 16 and thus is disposed over shell 16. In some embodiments, the inner surface of coating 14 contacts the outer surface of shell 16. The contact between shell 16 and coating 14 may occur between portions of shell 16 and coating 14 or may be continuous. Coating 14 preferably encapsulates shell 16.

Coating 14 preferably includes inner and outer surfaces that each are spherical. Alternatively, coating 14 may be defined by inner and outer surfaces where one or both surfaces has an alternative shape, such as cubical, cylindrical, hemispherical, elliptical, and the like. Each surface is preferably closed. The thickness of coating 14 preferably is defined as the difference between the outer radius and the inner radius, computed by subtracting the inner radius from the outer radius. The inner radius is half the average diameter of the inner surface. Likewise, the outer radius is half the average diameter of the outer surface.

Coating 14 preferably includes a protective material. When particle 10 has a plasmon resonance associated with shell 16, the protective material is preferably one for which coating 14 does not shift peak wavelength 60 by more than about 20 nanometers. The protective material is preferably any substrate material suitable for forming core 15. Thus, coating 14 preferably provides a surface suitable for further layering of an additional shell. Further, the protective material preferably confers improved thermal stability to particle 10 with respect to a comparable particle excluding a coating. The comparable particle has a core having the same composition and size as core 15. Further, comparable particle 24 has a shell having the same composition and thickness as shell 16.

In some embodiments, coating 14 is sufficiently thick such that peak wavelength 60 is stable to at least about 300° C. Peak wavelength 60 is preferably stable within about 3%. In particular, peak wavelength 60 preferably varies by not more than about 3% when the conditions of particle 10 include a temperature between 20° C. and 300° C. In an exemplary arrangement, it is known that when core 15 is about 140 nanometers and shell 16 is about 30 nanometers, a thickness between about 60 and about 70 nanometers is sufficient such that peak wavelength 60 is stable to at least about 300° C. It is believed by the present inventors that a thickness of as little as about 25 nanometers would be sufficiently thick such that peak wavelength 6O is stable to at least about 300° C. for particle 10 having the a similarly sized core and a similarly thick shell. Further, stability to 600° C. has been observed for particles having coatings of about 60 nanometers.

It will be understood that any thickness of coating 14 will infer enhanced stability, with the plasmon resonance being stable at higher temperatures for thicker coatings. Coating 14 preferably has a thickness between about 5 nanometers and about 500 nanometers, more preferably between about 5 nanometers and about 200 nanometers.

Figure 5:
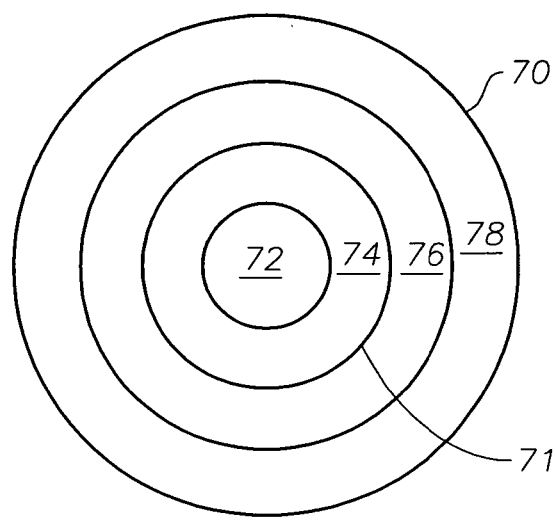
FIG. 5 is a cross-sectional view of a particle according to an alternative embodiment of the present invention.

Referring now to FIG. 5, in some embodiments, a particle 70 includes a subparticle 71, a coating 76, and a second shell 78. Subparticle 71 preferably includes a core 72 and a first shell 74. Core 72 may have any feature accorded core 15 above. Further, each of shells 74, 78 may have any feature accorded shell 16 above. Still further, coating 76 may have any feature accorded coating 14 above. Particle 70 may include an intermediate layer (not shown) between coating 76 and second shell 78. The intermediate layer may have any feature accorded intermediate layer 24 above.

Subparticle 71 is preferably a metal nanoshell that includes a spherical dielectric core surrounded by a thin metallic shell. For metallic materials for which particle 70 has a plasmon resonance. The geometrical dimensions of the shell dictate the plasmon resonance. The plasmon resonance of a single-shell metal nanoshell can be tuned in a range at least from the visible to the mid-infrared spectrum. Utilizing a multi-layer geometry has the advantage that a second plasmon resonance of the particle can be tuned at least across the mid-infrared region of the spectrum. Further, the presence of a second metal shell preferably enhances the plasmon resonance associated with a first metal shell.

When particle 70 has a second plasmon resonance associated with second shell 78, the presence of second shell 78 provides the ability to position the second plasmon resonance of particle 70 associated with second shell 78 at a peak wavelength red-shifted with respect to a comparable particle having a size the same as the average distance across shell 78 between opposite sides. Thus, for the same size net particle, a more red-shifted plasmon resonance is possible.

Figure 6:
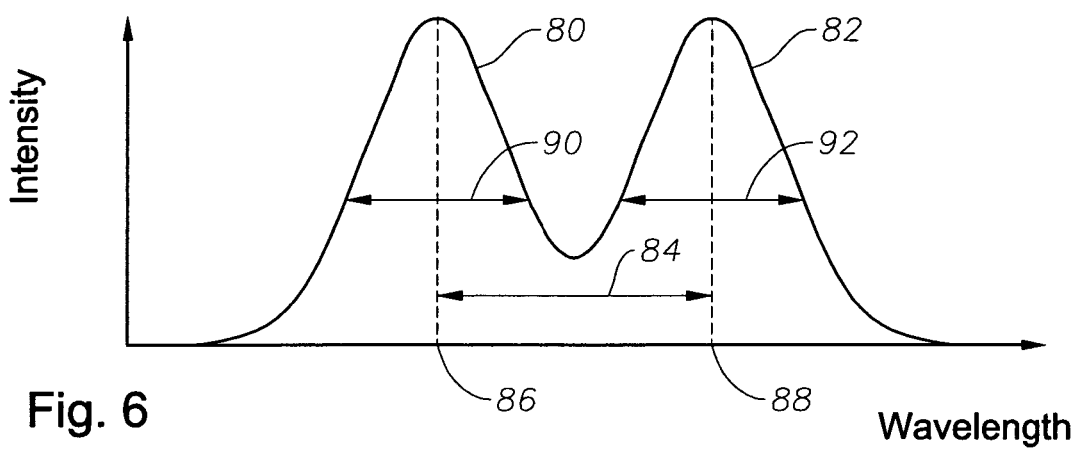
FIG. 6 is a schematic plot of a spectrum associated with a particle as shown in FIG. 3.

Referring now to FIG. 6, in some embodiments, when particle 70 has a first plasmon resonance peak 80 associated with first shell 74 and a second plasmon resonance peak 82 associated with second shell 78, plasmon resonances 80, 82 are spectrally distinct. More particularly, the peak difference 84 between peak wavelengths 86, 88 is preferably greater than half the sum of peak widths 90, 92. Each of peak widths 90, 92 is a full width half maximum of corresponding plasmon resonance 80, 82. Peak wavelength 88 is preferably between about 300 nanometers and about 20 microns, more preferably between about 0.7 microns and about 20 microns. Coating 76 preferably has a thickness between about 5 nanometers and about 500 nanometers, more preferably between about 5 nanometers and about 200 nanometers.

Referring again to FIG. 1, it will be understood that core 15 may alternately be a composite particle that includes a solid core and at least one shell. In this manner, referring also to FIG. 5, particle 10 may have a similar structure to particle 70. Further, it is contemplated that a particle, such as particles 10, 70, may include a core and any number of metallic shells. A metallic shell may be layered upon another metallic shell. Alternatively, and preferably, each pair of metallic shells is separated by a coating. In some embodiments, each shell is a conducting layer. Further, in some embodiments, each coating is a non-conducting layer. Exemplary non-conducting layers include dielectric materials. Alternatively or in combination, exemplary non-conducting layers include semi-conducting materials.

Methods for Making Multi-Layer Nanoshells

According to a preferred embodiment of the present invention, making a composite particle includes providing a subparticle that includes a core and a metallic shell and layering a coating on the shell. The method may further include layering a second metallic shell on the coating.

The subparticle is preferably a metal nanoshell that includes a core and a metal shell layered on the core. A method of providing a metal nanoshell may method for making a metal nanoshell previously disclosed in U.S. patent applications: Ser. No. 09/038,377, filed Mar. 11, 1998; Ser. No. 09/755,229, filed Jan. 5, 2001; Ser. No. 09/966,544, filed Sep. 27, 2001; and Ser. No. 09/965,305, filed Sep. 27, 2001, which are each incorporated herein by reference.

Layering a coating on the shell preferably includes purifying a solution of subparticles, functionalizing the subparticles, and coating the functionalized subparticles with a coating material. The coating is preferably protective against heat stress. Further, the coating material is preferably a nonconductive material such as a dielectric material or a semiconducting material.

A subparticle is preferably functionalized by modifying the surface of the subparticle to create a functionalized subparticle capable of binding a coating material. The method of functionalization may vary according to the chemical identity of the shell of the subparticle and on the chemical identity of the coating material.

For metallic shells and silica coatings, according to an embodiment of the present invention, functionalizing a subparticle includes binding a linker molecule. The linker molecules are preferably hydrolyzed APTES.

Thus, according to an embodiment of the present invention, a method for making a composite particle includes providing a metallic nanoshell particle and growing a coating layer onto the particle. The metal nanoshell particle preferably includes a dielectric core surrounded by a first metallic shell.

Further, according to an alternative embodiment of the present invention, a method for making a composite particle further includes providing a metal nanoshell particle having a first shell layer and forming a second shell layer over the particle. The method preferably further includes growing a coating layer onto the particle, and growing the second shell layer onto the coating layer.

Providing a Metal Nanoshell Subparticle

According to an embodiment of the present invention, a method for making a nanoshell includes providing a silica core, and growing a gold shell on the silica core. The gold shell is grown on the silica core using aminopropyltriethoxysilane molecules to generate linker molecules that functionalize the core. Growth of the gold shell includes attaching gold colloidal particles to the linker molecules and reducing additional gold from solution onto the gold colloidal particles. Preferably the method is carried out in solution. The method preferably includes providing a solution of the gold colloidal particles. The method preferably further includes aging the solution of gold colloidal particles. The time period of aging is from about 5 to about 30 days, more preferably from about 7 to about 24 days, still more preferably from about 10 to about 20 days. The aging is preferably carried out under refrigeration, preferably at a temperature of about 40° F. (about 4° C.).

According to an embodiment of the present invention, monodisperse silica cores are grown using the Stöber method, described in W. Stöber, et al. Journal of Colloid and Interface Science 26, pp. 62–69 (1968), hereby incorporated herein by reference. In particular, tetraethylorthosilicate (TEOS), ammonium hydroxide ($NH_4OH$), and water are added to a glass beaker containing ethanol, and the mixture is stirred overnight. The size of the Stöber particles is dependent on the relative concentrations of the reactants. These particles are then functionalized with 3-aminopropyltriethoxysilane (APTES). The 3-aminopropyltriethoxysilane (APTES) hydrolyzes to form a 3-aminopropylsilanetriol linker molecule. The silane group attaches to the silica surface, and the amine group is exposed.

It will be understood that alternative cores includes any core as described above in the section entitled Multi-Layer Nanoshells. Further, alternative linker molecules that may be attached to the core to functionalize the core include any linker molecule as described above in the same section.

According to an embodiment of the present invention, ultrasmall gold colloid (1–3 nm) is synthesized using a recipe reported by Duff, disclosed in D. G. Duff, et al., Langmuir 9, pp. 2310–2317 (1993), hereby incorporated herein by reference. This entails, for example, a solution of 45 mL of water, 1.5 mL of 29.7 mM $HAuCl_4$, 300 uL of 1M NaOH and 1 mL (1.2 mL aqueous solution diluted to 100 mL with water) of tetrakishydroxymethylphosphoniumchloride (TBPC). This gold is then added to the functionalized silica particles, preferably after aging as described above. The gold colloid attaches to the amine-terminated silica particles, which provide nucleation sites for the chemical deposition of a metallic shell.

It will be understood that, alternatively, any metal that can be made in colloidal form could be attached as a metal cluster. For example, silver, platinum, palladium, lead, and the like could be used.

Further, according to an alternative embodiment of the present invention, a method of making a metal nanoshells includes providing an intermediate layer of a functionalizing metal. The functionalizing metal is preferably tin. Alternatively, the functionalizing metal is titanium. Tin functionalization is described in U.S. patent application Ser. No. 09/965,305, filed Sep. 27, 2001. As disclosed therein, functionalization with gold colloid attached to a linker molecule attached to a substrate, as described above, may be replaced by tin functionalization, as described below. In this way, nanoshells each having a layer of a shell metal may be made by mixing tin ions and substrate particles in solution to form functionalized particles, followed by reduction of the shell metal onto the functionalized particles.

As further disclosed in U.S. patent application Ser. No. 09/965,305, filed Sep. 27, 2001, after separation from a reactant solution, such as by centrifugation, Stöber particles are redispersed in a first solvent and submerged in a solution of $SnCl_2$ in a second solvent. The first solvent may be water. Alternatively, and more preferably, the solvent is a methanol/water mixture, preferably 50% by volume methanol. Further, the second solvent may be water. Alternatively, and preferably the second solvent is a methanol/water mixture, preferably 50% by volume methanol. A solution of tin chloride in a methanol/water solvent preferably includes a surfactant, such as $CF_3COOH$. A method of tin functionalization using a methanol/water solvent is described, for example in Yoshio Kobayashi, et al. Chemical Materials 13, pp. 1630–1633 (2001), hereby incorporated herein by reference. By adding tin (II) chloride $SnCl_2$ and Stöber nanoparticles in a solvent, it is believed that tin atoms are deposited chemically onto the surface of the Stöber nanoparticles. Small tin precursor particles (<2 nm) form on the surface of the silica nanoparticle upon addition of more $SnCl_2$ to the solution. Presence of these tin particles have been observed by TEM, for example as described in Example 17 below.

As still further disclosed in U.S. patent application Ser. No. 09/965,305, filed Sep. 27, 2001, after a period of time, such as at least 45 minutes, the tin-functionalized silica particles are separated from solution and redispersed in water. The separation from solution is achieved on the lab bench scale by centrifugation. Centrifugation has the advantage of removing any excess tin and preparing the tin-coated nanoparticles for further metal reduction. When the functionalized particles are redisbursed in water the pH tends to be about 3. The pH is preferably modified, such as to at least 9 for subsequent reduction of silver. Modification of the pH has the advantage of achieving reaction conditions favorable for reduction of a shell metal.

Reduction of shell metal preferably includes mixing a functionalized dielectric substrate, a plurality of metal ions, and a reducing agent, in solution. Formaldehyde is a preferred reducing agent. The metal may be any shell metal as disclosed above in the section entitled Multi-Layer Nanoshells.

When the metal is selected from among silver, copper, and nickel, as disclosed in Ser. No. 09/966,544, filed Sep. 27, 2001, the method preferably further includes raising the pH of the solution effective to coat the substrate with the metal. In particular, in one embodiment, as disclosed therein, gold-functionalized silica particles are mixed with 0.15 mM solution of fresh silver nitrate and stirred vigorously. A small amount (typically 25–50 microliters) of 37% formaldehyde is added to begin the reduction of the silver ions onto the gold particles on the surface of the silica. This step is followed by the addition of doubly distilled ammonium hydroxide (typically 50 micro-liters). The "amounts" or "relative amounts" of gold-functionalized silica and silver nitrate dictate the core to shell ratio and hence the absorbance. Before further use, the nanoshell solution is preferably centrifuged to separate the nanoshells from solution and thus remove byproducts and any solid silver colloid that formed. The nanoshells are preferably resuspended in a solvent. The solvent is preferably water. Alternatively, the solvent is ethanol. Centrifugation and resuspension may be repeated for a total number of cycles of preferably between 1 and 2.

Growing a Coating on the Subparticle

Growing a coating layer onto the particle preferably includes growing a thin layer of coating, and increasing the thickness of the coating. The dielectric core preferably includes silica, more preferably essentially silica. Further, the coating preferably includes silica, more preferably essentially silica. Attaching a linker molecule to the metal surface preferably functionalizes the particle. Attaching a linker molecule preferably includes adding an aminoalkoxysilane to a solution containing the metallic nanoshell particles, allowing the amino group to attach to the metal surface and exposing the silane group. Growing a thin layer of coating preferably includes condensing silicate onto the surface of the functionalized particle, preferably from a solution containing a silicate salt, more preferably a solution of sodium silicate. Increasing the thickness of the coating preferably includes growing the coating by the Stöber method, that is by adding tetraethylorthosilicate (TEOS), and ammonium hydroxide ($NH_4OH$) to a solution containing thinly coated particles, preferably in an ethanol solvent.

The nanoshell surface is preferably functionalized using a silane molecule that can attach to the metal. The functional molecule that is attached to the metal surface could be any molecule where one end group is amenable to attachment at the metal surface leaving the opposite silane group exposed. The silane is preferably an aminoalkoxysilane molecule. Thus, particles with a metallic shell can be functionalized using an aminoalkoxysilane molecule. The aminoalkoxysilane is preferably aminopropyltriethoxy silane (APTES.) The amino group attaches to the metal surface and the silane group is exposed for further functionalization.

A thin silica layer can then be grown onto the metal surface using the aminoalkoxysilane-functionalized surface. The silica layer is preferably grown by first condensing a thin layer using the sodium silicate solution. This limits the minimum thickness of the silica layer. A thin silica layer can then be grown onto the metal surface using the aminoalkoxysilane-functionalized surface. A 0.54% wt solution of sodium silicate, adjusted to pH=9–11, is added to the functionalized nanoshell particles. The silicate condenses onto the surface forming a thin silica layer. The thickness of this silica layer can be increased using the Stöber method of silica particle growth.

The present inventors discovered that improved results for subsequent coating of the subparticles were obtained by first purifying the solution of subparticles. The purification is preferably effective to remove excess ions in solution that could interfere with the APTES and silicate deposition in later processes. Preferably, the purified solution contains less than about 7 mM excess ions.

Growing a Second Metallic Shell on the Coating

After growth of the silica layer to a desired thickness a second metal shell can be grown using the same method used for growing a first shell to provide a metallic nanoshell particle.

The metal shell can be any metal that has been previously disclosed as being used in the synthesis of metal nanoshells. The growth of the metal shell can be facilitated by any of the previously disclosed methods.

In one embodiment, growing a second shell includes attaching APTES to the coating, attaching gold colloids to the APTES, and reducing additional gold onto the gold colloid. The present inventors discovered that improved results for subsequent seeding with gold colloid, and growth of the second shell were obtained by bringing a solution of a coated particle and APTES to a rolling boil in ethanol, preferably at a temperature of about 70° C.

Without further elaboration, it is believed that one skilled in the art can, using the description herein, utilize the present invention to its fullest extent. The following specific embodiments are to be construed as illustrative and not as constraining the scope of the present invention in any way whatsoever.

EXAMPLES

Example 1

Providing a Subparticle Having a Silica Core and a Gold Shell

Silica particles were grown using the Stöber method, described in W. Stöber, et al. Journal of Colloid and Interface Science 26, pp. 62–69 (1968), which is incorporated herein by reference. The silica particles produced each had a spherical shape, were approximately uniform in size, and had a standard deviation of less than 10% (4% is routinely achievable). Tetraethyl orthosilicate (TEOS) 99.999% was obtained from Aldrich Chemical Co., sodium hydroxide was from Fluka Chemical Co. and highly purified water was obtained from a Millipore "TOTALQ" system that included "MILLIQ$^{UV}$" and "MILLIQ$^{RO}$" filters. All glassware was cleaned with chromic acid solution and thoroughly rinsed with "TOTALQ" water.

Variations in base concentration, and TEOS concentration were used to produce monodisperse silica spheres of various sizes. Temperature and electrolyte concentration also affected the final diameter of the particles. Generally, the following concentration ranges were used: 0.1 to 0.5 M TEOS, 0.5 to 17 M $H_2O$, and 0.5 to 3.0 M ammonia. In addition, a variety of alcohols were used as solvents, however, ethanol was preferred. Higher ammonia concentrations provide larger particles.

Uniform particles having a diameter of 120 nanometers as measured by a transmission electron microscope (TEM) were prepared by the following method. Approximately 50 milliliters (ml) of dry (100%) ethanol and 4 ml of $NH_4OH$ (25% $NH_3$ in water), were stirred in a glass beaker. To this solution, 2.2 ml of tetraethyl orthosilicate having a purity of at least 99.999% was added and allowed to stir for at least 8 hours. By varying the concentrations of $NH_4OH$, water and silicate among other factors, the size of the silica particle was varied from approximately 20 nanometers to 500 nanometers diameter. Larger core particles were grown using a seeded growth technique where additional TEOS and water were added to already formed silica particles. Multiple additions of small amounts of additional reactants allowed monodisperse core particles to be grown as large as 4 microns.

10 milliliters of a silica particle suspension such as prepared as described above, was added to a 50 milliliter glass beaker. Next, pure aminopropyltriethoxy silane (APTES) was added to the solution. Based on estimates, enough silane was added to coat the particles with multiple layers of silane. For example, 40 microliters of undiluted APTES was used for particles having diameters of 120 nanometers. The solution was stirred for 2 hours, diluted to 200 milliliters and then heated to a boil for four hours. The heating step promotes the reaction of silanol groups into Si—O—Si bonds and strengthens the attachment of the silane to the silica. This mixture was centrifuged at 2000× g for 30 minutes. The supernatant was decanted off and the pellet was redispersed ultrasonically. This washing procedure was repeated five times.

Metal clusters were attached to the linker molecules on the core by immersing the derivatized core particles in a metal colloid bath. Any metal that can be made in colloidal form could be attached as a metal cluster. For example, silver, platinum, palladium, lead and the like could be used. In addition, metal-like organic molecules are suitable. Such compounds include polyacetylene and polyaniline. Gold clusters having a diameter of 1–3 nanometers were grown using the reduction reaction as described by D. G. Duff, et al., Langmuir 9, pp. 2310–2317 (1993), which is incorporated herein by reference to the extent such methods are disclosed. A solution of 45 ml of water, 300 microliters of 1 M NaOH and 1 milliliter of a freshly diluted 1% aqueous solution of tetrakis(hydroxymethyl)phosphonium chloride (THPC) was stirred in a 100 milliliter flat bottom beaker with a pyrex coated magnetic stir bar. After 2 minutes, 2 ml of chloroauric acid (25 mM dark-aged stock solution, hydrogen tetrachloroaurate (III) trihydrate 99.999% from Aldrich) was added. This reaction mix was used to form gold particles in solution with an average particle diameter of 1–2 nanometers. To increase the size of the particles, higher concentrations of gold chloride could be used. Particles prepared in this fashion were referred to as ultra small gold particles or (UG).

Generally, the UG solution was mixed with silica particles in an amount that would theoretically cover the core particle surface five to ten times. The solution was allowed to react for 3 hours under gentle stirring. In the preferred embodiment the gold was used 5–30 days after it was made.

Typically, after three hours, unreacted gold colloid was separated from the gold-decorated silica particles by centrifugation at 1000 RCF. The minimum amount of centrifugal force required to effect separation was used to avoid coalescence of the particles. Particles were washed twice by resuspension and centrifugation.

Deposition of gold proceeded using a variety of reducing agents such as hydroxylamine hydrochloride, sodium borohydride, and formaldehyde. Formaldehyde was preferred. In one example, a solution of 25 mg anhydrous potassium carbonate was added to 100 milliliters of water containing 1.5 milliliters of 25 mM chloroauric acid solution (PCG). This solution was allowed to age in the dark for one day. Approximately 10 milliliters +/−5 milliliters of PCG was rapidly stirred with 2–5 milliliters of the gold clustered silica solution. A 100 microliter aliquot of freshly prepared formaldehyde solution (2% by volume in water) was slowly added.

Example 2

Forming a Silica Coating

A solution of subparticles each having a silica core and a gold shell was prepared using APTES to functionalize silica cores, attaching gold colloid to the silica cores, and reducing additional gold onto the gold colloids. This method is exemplified in Example 1 above. It has been observed that a silica coating can be grown on a subparticle having a partial shell just as easily as on a subparticle having a complete shell.

Purifying the subparticle solution included performing dialysis on the solution. Between about 20 and about 40 mL of a dilute aqueous subparticle solution having a concentration between about $10^8$ and about $10^{10}$ particles/ml. The ultrapure water was Milli-Q water with no additives. This water was de-ionized and uv-irradiated. This water tended to be slightly acidic, that is with a pH between about 5 and about 7. The concentration of the subparticle solution was not observed to effect the dialysis process for concentrations in the range of $10^8$ to $10^{10}$.

The dialysis included containing the dilute solution in a 6 kD–8 kD molecular weight cut-off (MWCO) dialysis tubing in the form of a Spectra/Por$^{TR}$ regenerated cellulose membrane, available from Spectrum$^{TR}$ Laboratories. This tubing contains about 6.5 mL of solution to about 1 cm of tubing. A magnetic suspended bag set-up was used in conjunction with the tubing. This set-up has the advantage that it agitates the subparticle solution enough to keep the subparticles better suspended during the process. Without sufficient agitation, the subparticles tend to fall out very early in the dialysis process and this tends further to result in subsequent poor silica growth. The standard clips, available as Spectra/Por$^{TR}$ Standard Closures from Spectrum$^{TR}$ Laboratories were used to seal the bag leaving a small air pocket at the top of the bag (e.g. about 1 cm). The volume of the reservoir was ×100 the volume of the dilute solution. Alternatively, having a ratio of solution volume to reservoir volume of 40 mL:2000 mL was observed to produce no appreciable drop off in effectiveness.

The concentration of the purified solution of suparticle solution was determined by UV/Visible Spectroscopy. This concentration was entered into a customized Excel spreadsheet in order to compute apredetermined amounts of silicate for coating the subparticles and APTES for functionalizing the subparticles. The predetermined amount of APTES was a slight excess over the amount associated with the formation of a monolayer of the functionalizing reactant. The predetermined amount of silicate was at least enough to form a 4 nanometer thick coating of silica. It was observed that if either amount was off by an order of magnitude or more then results of the silica growth process were unpredictable.

The method used for coating the subparticle with silica was based on the method for coating a solid gold core with silica disclosed in L. M. Liz-Marzan, et al., Langmuir 12, 4329–4335 (1996), hereby incorporated herein by reference.

Functionalizing the subparticles included mixing a solution of subparticles with a solution of APTES. APTES (at least 100 μL) was used to prepare a 1 mM solution of APTES in Milli-Q water (4.70 μL APTES to 20 mL water). The subparticle solution was removed from the dialysis and any flocculated subparticles were redispersed by gently rolling the bag between a person's fingers. The bag was preferably rinsed with Milli-Q water to make sure all the subparticles are removed. The subparticle solution was returned to a centrifuge tube and probed for ~30 s. The subparticles were preferably used within 12 hours of completing the dialysis as some permanent flocculation may begin if the subparticles are left to stand too long. The subparticle solution was transferred to clean beaker and stirring begun with a stir-bar. The pH of the subparticle solution was checked. The pH of a subparticle solution tends to be about 5. If the pH was not about 5, the pH was adjusted to about 5. A predetermined amount of 1 mM APTES solution was added, where the amount was as determined from a spreadsheet program, as described above. The solution was stirred for about 1 min and allowed to stand for 15 min. The solution was transferred to a centrifuge tube and washed at least once using the same centrifuge speed as used for the unfunctionalized subparticles. The subparticles were redispersed in Milli-Q water and probed for ~30 s.

A silicate solution was prepared in advance. In particular, a 0.54% wt solution of sodium silicate ($Na_2SiO2$) at pH=9–11 was prepared. An aliquot of about 27% wt $SiO_2$ was diluted to a desired volume. A 20 mL volume was found to be adequate for several months of laboratory scale preparations of coated subparticles. The pH was adjusted by adding scoops, with a spatula, of an ion exchange resin (IXR, basic, amberlite, prepared earlier), shaking the solution, and letting the solution stand until the beads settled. A pH meter or paper was used to measure the pH. This process was repeated until the desired pH was reached. If the pH was overshot, a very small amount (e.g.<10 µL) of 1 M HCl was added to bring the pH back down. Once the desired pH range was reached, the beads were allowed to settle out and the solution removed by pipette. The solution was run through a syringe filter to make sure there was no large particulate matter left from the IXR.

Coating the subparticles included mixing a solution containing functionalized subparticles with a solution of sodium silicate. A solution of functionlized subparticles was transferred to a beaker and stirring begun with a stir-bar. The appropriate amount of a 0.54% wt silicate solution was added, as determined from spreadsheet as described above. The resulting solution was stirred for about 1 mm. The solution was transferred to dialysis tubing and dialysis was carried out for 24 hrs using the magnetic suspended bag set-up with a fresh reservoir of Milli-Q water. It is believed that the dialysis tends to remove excess silicate that is not depositing on the subparticle's surface. This has the advantage of tending to prevent excess silicate from forming residual silica particles in solution and reduce silica particles growing together. After 24 hrs. the solution of coated particles was removed from the dialysis bag. Any flocculated particles were redispersed by gently rolling the bag between a person's fingers. The bag was preferably rinsed with Milli-Q water to make sure all the particles were removed. The particles were washed in a centrifuge at least 2 times. It was observed that a way to tell if the process was successful is during the wash cycle. Particles with a thin silica layer tended not to flocculate from using too high a centrifuge speed. Thus, coated particles redispersed more easily than uncoated particles. The coated particles tended to have a thin silica coating of about 4–8 nanometers.

The particles were redispersed in ethanol to grow a thicker silica shell. The present inventors have observed that the initial thin silica coating does not have to be complete to get a good, thick silica coating. Further, the present inventors have noticed in TEM images that with partially grown metal shells silica can be seen on the metal islands. During seeded growth using the Stöber process, described in W. Stöber, et al. Journal of Colloid and Interface Science 26, pp. 62–69 (1968), which is incorporated herein by reference, the silica layer gets thicker and does coalesce to form a continuous silica shell. In the Stöber process, an ethanol solvent is used. It has been observed that this solvent tends to produce better results that an ethanol:water mixture in a ratio of 4:1. In a typical recipe, 20–40 mL sample of thin silica-coated particles in EtOH was diluted by 60–120 mL EtOH with 3–5 mL of $NH^4OH$ added and 0.5–1.1 mL of TEOS added. It was found that residual silica growth could be eliminated by slow addition of TEOS. Further, it was observed that an optimal growth pushed the limit of TEOS addition, and the resulting solution will have just the slightest hint of cloudiness to it. Such a solution had very small silica particles in it, but these were easily separated out in a thorough centrifuge wash process. The solution was stirred overnight at least 8 hours. The solution containing coated particles was centrifuged and redispersed in ethanol about 4–6 times. This had the advantage of tending to prevent formation of large particulate matter. When this matter was observed, it was almost a gel and the inventors believe that it is residual TEOS, small silica particles, or coated particles forming a gel. When it formed, the gel was separated by loosely packing a pasteur pipette with glass wool and filtering the particle solution through.

The above-described procedure was used to grow silica coatings having a thickness between about 10 nanometers and about 200 nanometers.

Example 3

Enhanced Thermal Stability of Silica-Encapsulated Metal Nanoshells

In this example, fabrication of silica layers onto completed gold nanoshells is described. A series of experiments on silica-encapsulated and uncoated gold nanoshells were conducted, where both their structural and optical properties were observed following heating cycles over a range of temperatures. It was observed that thick (50–70 nm) silica encapsulation layers greatly improved the thermal stability of gold nanoshells, preserving both the structural integrity of the metallic layer and the optical properties of the original nanostructure. For the silica-encapsulated nanoshells, an increase in thermal stability of more than 300 degrees Celsius, relative to uncoated nanoshells, was observed. The effectiveness of this thermally-stabilizing silica layer was observed to be dependent on its thickness: fissures that seemed to appear frequently in thinner layers appeared to compromise the encapsulation, and thus the thermal stabilizing effect of the layer.

Gold nanoshells were fabricated using a multi-step process that allowed for independent control over the core size and shell thickness. Silica nanoparticles were made using the Stöber method, as described in W. Stöber, et al. Journal of Colloid Interface Science 26, pp. 62–69 (1968), hereby incorporated herein by reference. These particles were then functionalized with 3-aminopropyltriethoxysilane (APTES). Small gold colloid was attached to the functionalized silica particles and gold was reduced onto these seeded particles, which caused the small gold colloid to grow larger and coalesce into a shell. The gold nanoshells were modified by the growth of a silica layer on the surface of the particle, using a procedure developed initially for the encapsulation of small gold colloid. This procedure is described T. Ung, et al., Langmuir 14, 3740–3748 (1998), hereby incorporated herein by reference.

A surprising result of the present inventors was the discovery that use a solution of nanoshells as typically prepared for spectroscopic analysis resulted in poor formation of a silica coating when using the procedure as described by T. Ung. The inventors discovered that improved results were obtained by passing the nanoshell solution first through dialysis. It is believed that this eliminated impurities remaining from the nanoshell synthesis after standard separation cycles of centrifugation and resuspension.

Figure 7:
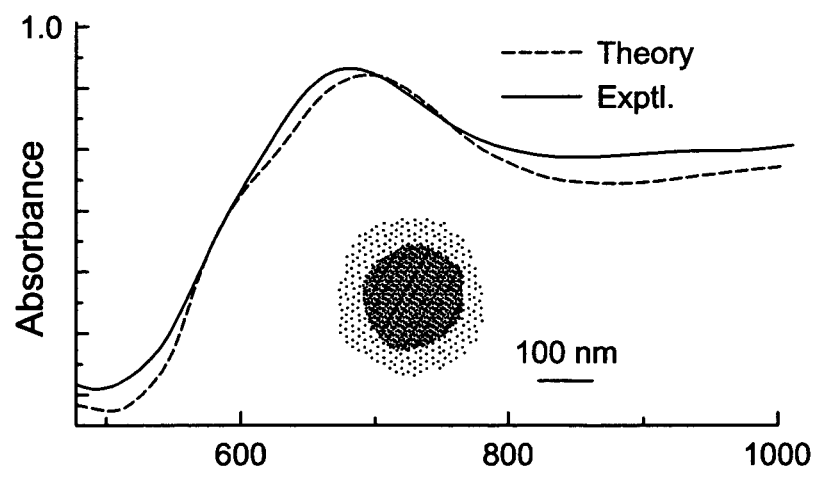
FIG. 7 is a plot of an absorbance spectrum for an exemplary particle having a silica core, a gold shell, and a silica coating.

FIG. 7 shows a typical absorbance spectrum for an aqueous solution of gold nanoshells coated in a thick silica layer. The spectrum is dominated by the peak at 700 nm, which, when compared to Mie scattering theory for the equivalent core-shell geometry, can be attributed to the quadrupole resonance of the metal shell. The absorbance shoulder, which extends from this feature to longer wavelengths in the near infrared, can be attributed to the dipole resonance of the metal shell. The dipole resonance for these core and shell dimensions occurs at 1105 nm (beyond the spectral range of the spectrometer used). The inset in FIG. 7 is a transmission electron microscope image of an approximately 200 nm diameter gold nanoshell particle with an approximately 60 nm thick silica layer. Particles of this size were used in obtaining the spectrum shown in FIG. 10. In particular, the nanoparticles had an average silica core diameter of 140 nm and an average shell thickness of 30 nm.

Figure 8:
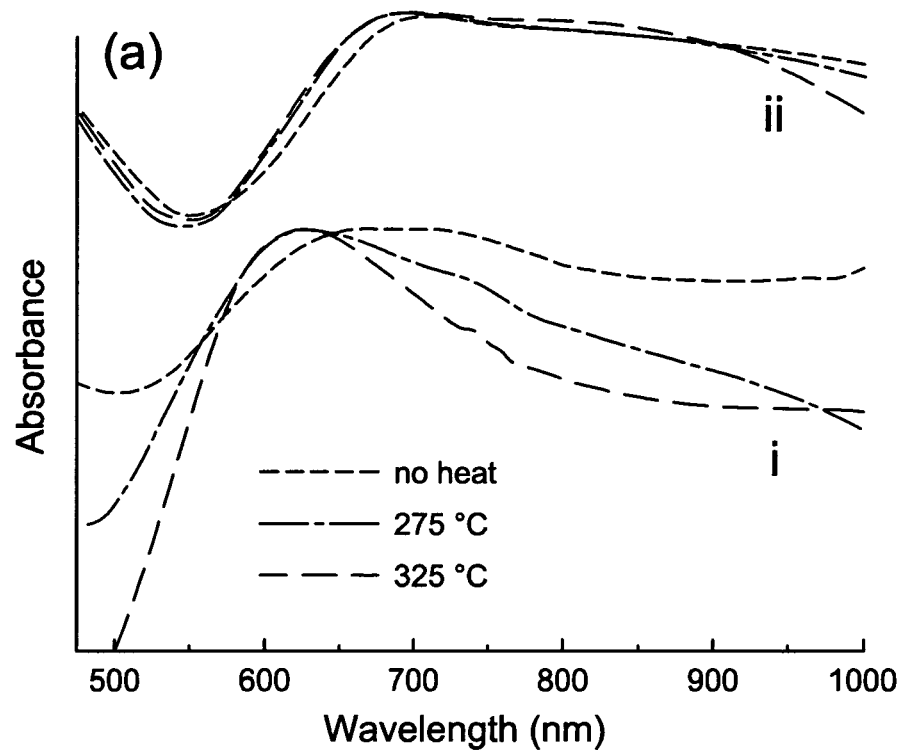
FIG. 8 contains plots of spectra obtained from exemplary particles having no coating, a thin coating, and a thick coating.
Figure 8:
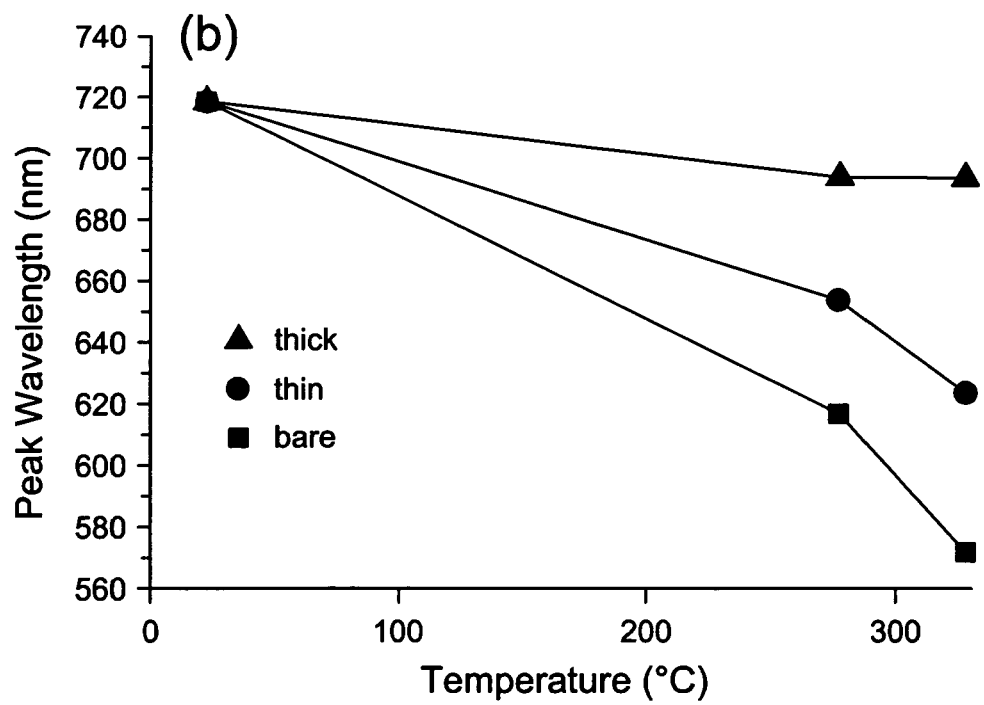

It was experimentally determined that uncoated gold nanoshells began to melt when subjected to a 2–3 hour heating cycle at 275° C. and were completely destroyed following exposure to a 2–3 hr heating cycle of 325° C. By heating cycle is meant that the temperature was raised to the temperature indicated, e.g. 275° C., and held for the indicated amount of time, e.g. 2–3 hr, and allowed to return to room temperature. The temperatures of 275° C. and 325° C. are both significantly below the bulk gold melting temperature of 1064° C. The gold shell was observed to melt at even lower temperatures when cycled for a longer time period, for example when heated at 175° C. for 12 hours. FIGS. 8(a) and 8(b) show results or testing of uncoated and coated nanoparticles having a core diameter of 140 nm and a shell thickness of 30 nm. FIG. 8(a) displays a set of nanoshell extinction spectra where the changes in absorbance following these heating cycles are shown. FIG. 8(a.i) shows spectra of gold nanoshells coated with a 6–8 nm layer of silica. This layer is referred to herein as a thin coating. Following a 3 hour heating cycle at 275° C., the broad maximum of the nanoshell spectrum originally observed at ~720 nm had shifted to 655 nm and was significantly narrower, suggesting that the shell nanostructure had experienced some changes in morphology. A further heating cycle to 325° C. revealed a further shift in the spectral peak of the optical response. In contrast, nanoshells encapsulated in a 60–70 nm silica layer, referred to herein as a thick coating, experienced only minor modifications in their optical response following heating cycles at 275° C. and 325° C. There is an overall spectral shift of only 20 nm during the initial heating cycle, as seen in FIG. 8(a.ii). This suggests that only minor changes in the nanoshell morphology may have occurred while cycling to this temperature. Further, the spectral shift observed in the initial heating cycle at 275° C. may be due to changes in the index of refraction of the thick silica encapsulant upon heating, such as $H_2O$ elimination and further condensation of —OH dangling bonds within the silica network. Virtually no changes in this spectrum were observable between the first and second heating cycle of the sample. In FIG. 8(b) the wavelength of the absorbance peaks shown in FIG. 8(a) is plotted against temperature for each of bare, thin-coated and thick-coated nanoshells. It can be seen in FIG. 8(b) that the absorbance peak for bare gold nanoshells shifts approximately 100 nm when heating from room temperature to 275° C. and shifts a further 50 nm when heated to 325° C. This change in the peak absorbance wavelength can be attributed to melting and destruction of the gold shell.

Figure 9:
FIGS. 9(a), 9(b), and 9(c) contains SEM images of exemplary particles after heating, the particles having no coating, a thin coating, and a thick coating.

FIG. 9(a), 9(b), and 9(c) reveals a set of scanning electron microscope (SEM) images that show the specific structural changes in nanoshell morphology for all samples, following the second heating cycle to 325° C. In FIG. 9(a), the uncoated nanoshells are shown: it is clearly evident that the shell layers were destroyed following the heating cycle to 325° C. The result of melting the gold shell was the formation of large, round gold nanoparticles that no longer coat, but remain attached to, the core silica nanoparticles. This agrees with the observed changes in the extinction spectrum following both heating cycles: the final peak position for the uncoated gold nanoshells occurred at approximately 570 nm, which is typical for large gold colloid.

This behavior is consistent with the morphology of the gold shell layer in the nanoparticles used for this example. The gold shell layer was formed by electroless deposition onto a colloid-coated silica nanoparticle surface. The initially formed nanoshell layer was thus composed of multiple domains. Such shell layers may even exhibit fissures and cracks that are visible in TEM images of the completed shells. Since melting is initiated at defects and grain boundaries, it is believed that multiple melting initiation sites occur, resulting in coverage of several large spherical gold clusters on the silica nanoparticle surface once the thermal cycling was complete. FIG. 9(b) shows gold nanoshells encapsulated within a thin (6–8 nm) silica layer. These particles began to melt at the visible fissures, but remained predominantly intact after being exposed to heat at 325° C. This result suggests that the thin silica coating existed primarily on the gold and did not necessarily span, that is, extend over, the fissures. The partially increased resilience of the gold shell at elevated temperatures may then be attributed to the presence of the thin silica layer, which partially stabilized the gold layer, preventing it from melting completely and forming gold nanospheres. Finally, in FIG. 9(c) SEM images of gold nanoshells encapsulated with a (50 nm) thick silica layer are shown, following successive heating cycles at 275° C. and at 325° C. The morphology of the gold shell is visible in the SEM image through the thick silica layer, and it appears to be unaltered following both heating cycles, indicating that there was very minimal, if any, melting of the gold shell within the silica encapsulant. Thus, the inventors believe that the silica encapsulant stabilized the gold shell over the range of temperatures where an uncoated shell would begin to melt by binding to the external surfaces and features where melting could be initiated. Also, the interior silica-gold interface did not appear to have as dominant a role in initiating melting as the existence of the external surface. The surface free energy of the gold shell was decreased by the existence of the silica shell, therefore raising the melting point of the nanoscale gold shell structure. Further, in further studies these encapsulated nanoparticles remained unaltered under heating cycles up to 600° C.

In summary, a sufficiently thick (60–70 nm) silica encapsulation layer grown around a composite nanoparticle has the advantage of greatly enhancing the thermal stability of coated nanoparticles relative to corresponding uncoated nanoparticles. For the case of gold nanoshells, an increase in destructive melting temperatures of approximately 300 degrees relative to uncoated nanoshells was observed. This thermal stabilizing encapsulant layer greatly improves the robustness of Metal Nanoshells for optics and photonics applications, particularly in the context of high-power laser excitation, and may prove useful in preparing metal nanoshells for incorporation in other nanoscale photonic materials and nanostructures.

Example 4

Forming a Second Metallic Shell

About 1–2 mL of APTES was added to 10 mL of a solution of silica-coated nanoshells having a concentration between about $10^8$ and about $10^{10}$ particles/ml. This amount of APTES represented an excess of the amount needed for functionaliziation of about 0.01 µL. The excess arose from the lowest limit that could be reliably added by pipette of 0.5 µL. For each solution, the solvent was ethanol. The solution was stirred for 0.5 hour and rapidly boiled (<1 hr). The solution was topped off with ethanol to the original volume and rapidly boiled again. After a second boiling step the solution was allowed to cool and washed using centrifugation. It seems to be important to reach a rolling boil as well. Boiling was observed to start around 60° C. Best results for subsequent growth of a metallic shell were observed when the boiling temperature was about 70° C., such that the boil was a roiling boil.

In a comparison study, to a first solution of silica cores just enough APTES was added and to a second comparable solution of silica cores a large excess (>×1000) of APTES was added. Each solution was boiled, treated for seeding with gold colloids, and treated for growth of a gold shell. Each seed solution was identical. No difference was observed in seed coverage or shell quality. These results support the conclusion that a large excess of APTES may be used for the second functionalization without harming subsequent shell formation. Further, as described above, it was found that adding a large excess of APTES to silica-coated particles did not adversely effect subsequent shell formation when the boiling temperature was at least 70° C.

Seeding a functionalized silica-coated particle with gold colloid proceeded exactly as for seeding on a functionalized core, as described above in Example 1 above. Further, growth of a second shell proceeded as for growth of a first shell. It was observed that shells could be grown in reasonable dilutions of particles in potassium carbononate solution (at about $1e^8$ part/mL shells achieved with dilution of 900 uL in 2 mL). It was observed that if the second-shell seed solution is similar in concentration to a typical single-shell seed solution then the process works with no problems. The second shell growth was made easier by slightly diluting the seed solution (by 2 or 3), a procedure which has also been used when growing shells on large silica cores.

Example 5

Optical Properties of Two-Shell Particles

Calculations were performed for model particles using Mie theory. The model particles each included a core, a first shell, a coating and a second shell. All surfaces were assumed to be spherical, to give a geometry of concentric spheres defining the core, the first shell, the coating, and the second shell. The contribution of size-dependent scattering to the peak width was accounted for as described in R. D. Averitt, D. Sarkar, and N. J. Halas, Physical Review Letters 78, 4217–4220 (1997), hereby incorporated herein by reference. Results are shown in FIG. 10.

Figure 10A:
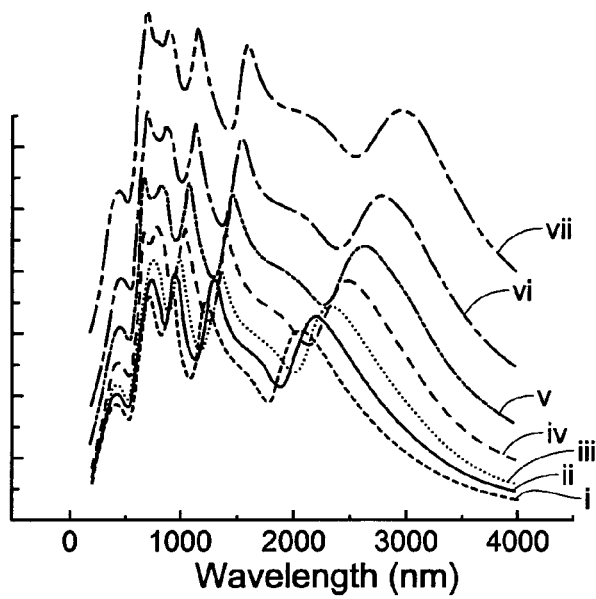
FIGS. 10(a), 10(b), and 10(c) contains plots of simulated spectra associated with exemplary particles having a silica core, a first gold shell, a silica coating, and a second gold shell.

For the plots in FIG. 10a an exemplary particle includes a silica core, a 15 nm thick gold shell, a 60 nm thick silica coating, and a 5 nm thick gold shell. The different spectra, i, ii, iii, iv, v, vi, and vii, shown are for particles having a core size of 300, 325, 350, 375, 400, 425, and 450 nm, respectively.

Figure 10B:
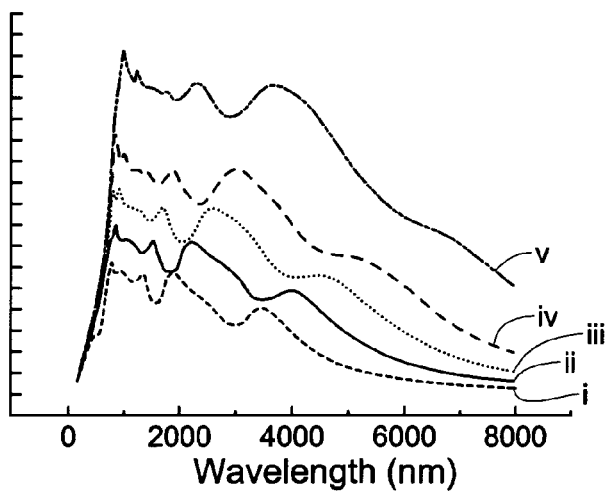

For the plots in FIG. 10b an exemplary particle includes a silica core, a 15 nm thick gold shell, a 60 nm thick silica coating, and a 5 nm thick gold shell. The different spectra, i, ii, iii, iv, and v, shown are for particles having a core size of 500, 600, 700, 800, and 1000 nm, respectively.

Figure 10C:
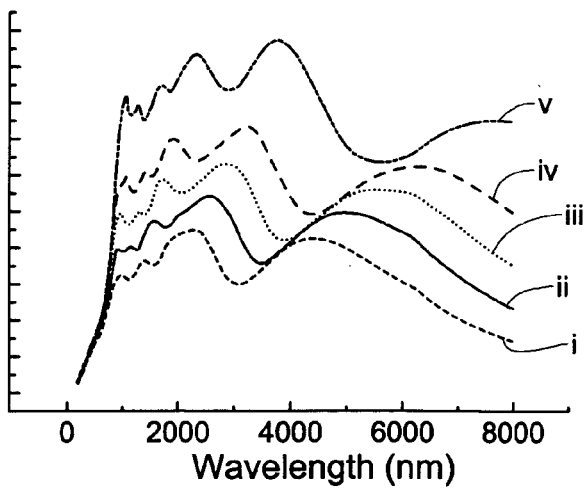

For the plots in FIG. 10c an exemplary particle includes a silica core, a 15 nm thick gold shell, a 200 nm thick silica coating, and a 5 nm thick gold shell. The different spectra, i, ii, iii, iv, and v, shown are for particles having a core size of 500, 600, 700, 800, and 1000 nm, respectively.

While preferred embodiments of this invention have been shown and described, modifications thereof can be made by one skilled in the art without departing from the spirit or teaching of this invention. The embodiments described herein are exemplary only and are not limiting. For example, unless otherwise indicated, the steps of a method may occur in any order. Many variations and modifications of the composition and method are possible and are within the scope of the invention. Accordingly, the scope of protection is not limited to the embodiments described herein, but is only limited by the claims that follow, the scope of which shall include all equivalents of the subject matter of the claims.

What is claimed is:

1. A nanoparticle, comprising:
   a functionalized core;
   a metallic shell layered on said functionalized core, wherein the functionalized core comprises a core and a functionalizing material, and wherein the functionalizing material comprises a metallic material; and
   a coating layered on said shell, wherein the coating does not shift a peak wavelength of plasmon tesonance associated with said shell by more than about 20 nanometers.

2. The nanoparticle according to claim 1 wherein said nanoparticle has a plasmon resonance associated with said metallic shell.

3. The nanoparticle according to claim 2 wherein said plasmon resonance has improved thermal stability with respect to a comparable nanoparticle excluding said coating.

4. The nanoparticle according to claim 3 wherein said coating is sufficiently thick such that said peak wavelength of said plasmon resonance is stable within 3% when exposed to a condition at least about 300° C.

5. The nanoparticle according to claim 3 wherein said coating is sufficiently thick such that said peak wavelength of said plasmon resonance is stable within 3% when exposed to a condition up to about 600° C.

6. The nanoparticle according to claim 1 wherein the thickness of said coating is between about 4 nm and about 200 nm.

7. The nanoparticle according to claim 1 wherein said coating comprises a material selected from the group consisting of silicon dioxide, titanium dioxide, polymethyl methacrylate, polystyrene, gold sulfide, cadmium selenium, cadmium sulfide, gallium arsenide, and dendrimers.

8. The nanoparticle according to claim 1 further comprising:
   a second metallic shell layered on said coating.

9. The nanoparticle according to claim 8
   wherein said nanoparticle has a first plasmon resonance associated with said first shell; and
   wherein said nanoparticle has a second plasmon resonance associated with said second shell.

10. The nanoparticle according to claim 9 wherein said coating has sufficient thickness such that said second plasmon resonance is spectrally distinct from said first plasmon resonance.

11. The nanoparticle according to claim 10
wherein said first plasmon resonance has a first peak wavelength and a first peak width;
wherein said second plasmon resonance has a second peak wavelength and a second peak width; and
wherein the difference between said peak wavelengths is greater than half the sum of said peak widths.

12. The nanoparticle according to claim 9 wherein said second plasmon resonance has a peak position between about 300 microns and about 20 microns.

13. The nanoparticle according to claim 9 wherein said second plasmon resonance has a peak position between about 0.7 microns and about 20 microns.

14. The nanoparticle according to claim 8 wherein the thickness of said coating is between about 5 nanometers and about 200 nanometers.

15. The nanoparticle according to claim 8 wherein said coating comprises a material selected from the group consisting of silicon dioxide, titanium dioxide, polymethyl methacrylate, polystyrene, gold sulfide, cadmium selenium, cadmium sulfide, gallium arsenide, and dendrimers.

16. The nanoparticle according to claim 1, wherein the functionalizing material comprises tin.

17. The nanoparticle according to claim 1, wherein the functionalizing material comprises titanium.

18. A nanoparticle comprising:
a functionalized core;
a shell surrounding said functionalized core, wherein the functionalized core comprises a core and a functionalizing material, and wherein the functionalizing material comprises a metallic material;
and a protective coating surrounding said shell, wherein the coating does not shift a peak wavelength of plasmon resonance associated with said shell by more than about 20 nanometers;
wherein said shell comprises a metal selected from the group consisting of silver, gold, nickel, copper, iron, platinum, and palladium.

19. The nanoparticle according to claim 18 wherein said protective coating comprises a dielectric material selected from the group consisting of silicon dioxide, titanium dioxide, polymethyl methacrylate, polystyrene, gold sulfide, cadmium selenium, cadmium sulfide, gallium arsenide, and dendrimers.

20. The nanoparticle according to claim 18 wherein the thickness of the coating is between about 4 nanometers and about 200 nanometers.

21. The nanoparticle according to claim 18 wherein said plasmon resonance has improved thermal stability with respect to a comparable nanoparticle excluding said coating.

22. The nanoparticle according to claim 21 wherein said coating is sufficiently thick such that said peak wavelength of said plasmon resonance is stable within 3% when exposed to a condition at least about 300° C.

23. The nanoparticle according to claim 18 further comprising:
a second shell surrounding said coating, wherein said second shell comprises a metal selected from the group consisting of silver, gold, nickel, copper, iron, platinum, and palladium.

24. The nanoparticle according to claim 23
wherein said nanoparticle has a first plasmon resonance associated with said first shell; and
wherein said nanoparticle has a second plasmon resonance associated with said second shell.

25. The nanoparticle according to claim 24 wherein said second plasmon resonance has a peak position of from about 0.7 microns to about 20 microns.

26. The nanoparticle according to claim 24 wherein said coating has sufficient thickness such that said second plasmon resonance is spectrally distinct from said first plasmon resonance.

27. The nanoparticle according to claim 26
wherein said first plasmon resonance has a first peak wavelength and a first peak width;
wherein said second plasmon resonance has a second peak wavelength and a second peak width; and
wherein the difference between said peak wavelengths is greater than half the sum of said peak widths.

28. The nanoparticle according to claim 26 wherein the thickness of said coating is at least about 5% of the diameter of said core.

29. The nanoparticle according to claim 26 wherein the thickness of said coating is between about 4 nanometers and about 200 nanometers.

30. The nanoparticle according to claim 18, wherein the functionalizing material comprises tin.

31. The nanoparticle according to claim 18, wherein the functionalizing material comprises titanium.

32. A nanoparticle comprising:
a functionalized core and a plurality of conducting shells, wherein at least one adjacent pair of shells is separated by a non-conducting layer, and wherein each said non-conducting layer comprises a material selected from the group consisting of silicon dioxide, titanium dioxide, polymethyl methacrylate, polystyrene, gold sulfide, cadmium selenium, cadmium sulfide, gallium arsenide, and dendrimers, and wherein the non-conducting layer is a coating surrounding a shell, wherein the coating does not shift a peak wavelength of plasmon resonance associated with said shell by more than about 20 nanometers, and further wherein the functionalized core comprises a core and a functionalizing material, and wherein the functionalizing material comprises a metallic material.

33. The nanoparticle according to claim 32 wherein said nanoparticle has a plasmon resonance associated with said at least one shell.

34. The nanoparticle according to claim 33 wherein said at least one shell comprises gold.

35. The nanoparticle according to claim 33 wherein said at least one shell comprises silver.

36. The nanoparticle according to claim 33 wherein said plasmon resonance has a peak wavelength in the infrared.

37. The nanoparticle according to claim 33 wherein said plasmon resonance has a peak wavelength between about 0.7 microns and about 20 microns.

38. The nanoparticle according to claim 32, wherein the functionalizing material comprises tin.

39. The nanoparticle according to claim 32, wherein the functionalizing material comprises titanium.

* * * * *